US012752066B2

(12) United States Patent
Maeda et al.

(10) Patent No.: US 12,752,066 B2
(45) Date of Patent: Oct. 6, 2026

(54) CPAP DEVICE

(71) Applicant: Murata Manufacturing Co., Ltd., Kyoto (JP)

(72) Inventors: Hiroki Maeda, Kyoto (JP); Atsushi Hattori, Kyoto (JP); Yoshio Yamanaka, Kyoto (JP); Yoshiro Konishi, Kyoto (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 601 days.

(21) Appl. No.: 18/347,866

(22) Filed: Jul. 6, 2023

(65) Prior Publication Data

US 2025/0010002 A1 Jan. 9, 2025

(51) Int. Cl.
*A61M 16/00* (2006.01)
*F04D 29/66* (2006.01)

(52) U.S. Cl.
CPC ....... *A61M 16/0066* (2013.01); *F04D 29/668* (2013.01); *A61M 2205/42* (2013.01)

(58) Field of Classification Search
CPC ...................... A61M 16/0066; A61M 16/0069
See application file for complete search history.

(56) References Cited

U.S. PATENT DOCUMENTS

| | | | | |
|---|---|---|---|---|
| 8,427,020 B2 | 4/2013 | Hoffman et al. | | |
| 2005/0069407 A1* | 3/2005 | Winkler | F03B 1/00 | 415/58.5 |
| 2007/0247009 A1* | 10/2007 | Hoffman | F04D 25/0606 | 310/43 |
| 2011/0277957 A1* | 11/2011 | Kuo | F04D 25/0613 | 165/69 |
| 2016/0184539 A1 | 6/2016 | Suzuki et al. | | |
| 2021/0001069 A1 | 1/2021 | Higashiyama et al. | | |
| 2023/0028015 A1* | 1/2023 | Maeda | F04D 29/66 | |

FOREIGN PATENT DOCUMENTS

| | | | | |
|---|---|---|---|---|
| JP | H06-294550 A | 10/1994 | | |
| JP | 2015-033522 A | 2/2015 | | |
| WO | 2019/189126 A1 | 10/2019 | | |
| WO | WO-2021205877 A1 * | 10/2021 | F04D 29/66 | |

OTHER PUBLICATIONS

International Search Report for PCT/JP2021/012221 dated May 18, 2021.

* cited by examiner

*Primary Examiner* — Bradley H Philips
(74) *Attorney, Agent, or Firm* — McDonald Hopkins LLC

(57) ABSTRACT

A blower of a CPAP device is housed inside a main body case of a CPAP device. The blower is roughly divided into a fan unit housing a fan therein, and a delivery tube, through which air sent from the fan passes. In the main body case, a first support member, a second support member, and a third support member are interposed between the main body case and the fan unit to support the fan unit. When viewed from a rotation axis of the fan, the first support member and the second support member are disposed to pinch the blower on the side of a connection point between the fan unit and the delivery tube relative to the rotation axis, and the third support member is located on the opposite side to the connection point between the fan unit and the delivery tube relative to the rotation axis.

14 Claims, 8 Drawing Sheets

CPAP DEVICE

BACKGROUND OF THE DISCLOSURE

Field of the Disclosure

The present disclosure relates to a continuous positive airway pressure (CPAP) device configured to send air inhaled into the device to the airway of a user.

Description of the Related Art

In a CPAP device described in Patent Document 1, a blower for sending out air is housed inside a main body case. A sound absorbing silencer is housed in the main body case. A passage for supplying air to the blower is defined inside the sound absorbing silencer. The sound absorbing silencer is formed in such a shape as to substantially wrap the entire blower. Further, the sound absorbing silencer is in contact with an outer surface of the blower and an inner surface of the main body case to support the blower inside the main body case.

Patent Document 1: Japanese Unexamined Patent Application Publication No. 2015-033522

BRIEF SUMMARY OF THE DISCLOSURE

When a support member for supporting the blower is interposed between the blower and the main body case as in the CPAP device described in Patent Document 1, the effect of suppressing vibrations and noise significantly depends on a contact position between the support member and the blower. In the CPAP device of Patent Document 1, no consideration is given to the effectiveness of a position at which the support member is disposed from the perspective of preventing the user from perceiving vibrations, noise, and the like. Accordingly, there is still room for improvement in this respect.

In order to solve the above problem, the present disclosure is a CPAP device including a main body case; a blower housed inside the main body case; and three or more support members interposed between the main body case and the blower, and configured to support the blower inside the main body case. The blower includes a fan unit housing a fan configured to send air by being rotated, and a delivery tube through which the air sent from the fan passes. In a view from a direction of a rotation axis of the fan, first and second support members of the above-mentioned support members are disposed to pinch the blower on a side of a connection point between the fan unit and the delivery tube relative to the rotation axis, and a third support member different from the first and second support members of the above-mentioned support members is disposed on a side opposite to the connection point relative to the rotation axis.

According to the above configuration, since the blower is supported by, at least, three of the first to third support members, it is possible to suppress the vibrations of the entire blower. Further, since the vicinity of the delivery tube in the blower is pinched with the first support member and the second support member, it is possible to more effectively suppress the vibrations of the delivery tube in the blower. In the case where the vibrations of the delivery tube are suppressed, it is also possible to suppress the transmission of the vibrations from the delivery tube to the user via a hose, a mask and the like, and therefore the user is unlikely to perceive the vibrations.

The user is unlikely to perceive the vibrations of a blower due to the drive of a CPAP device.

DETAILED DESCRIPTION OF THE DISCLOSURE

Hereinafter, an embodiment of a CPAP device configured to send air introduced into the device to the airway of a user will be described with reference to the accompanying drawings.

Figure 1:
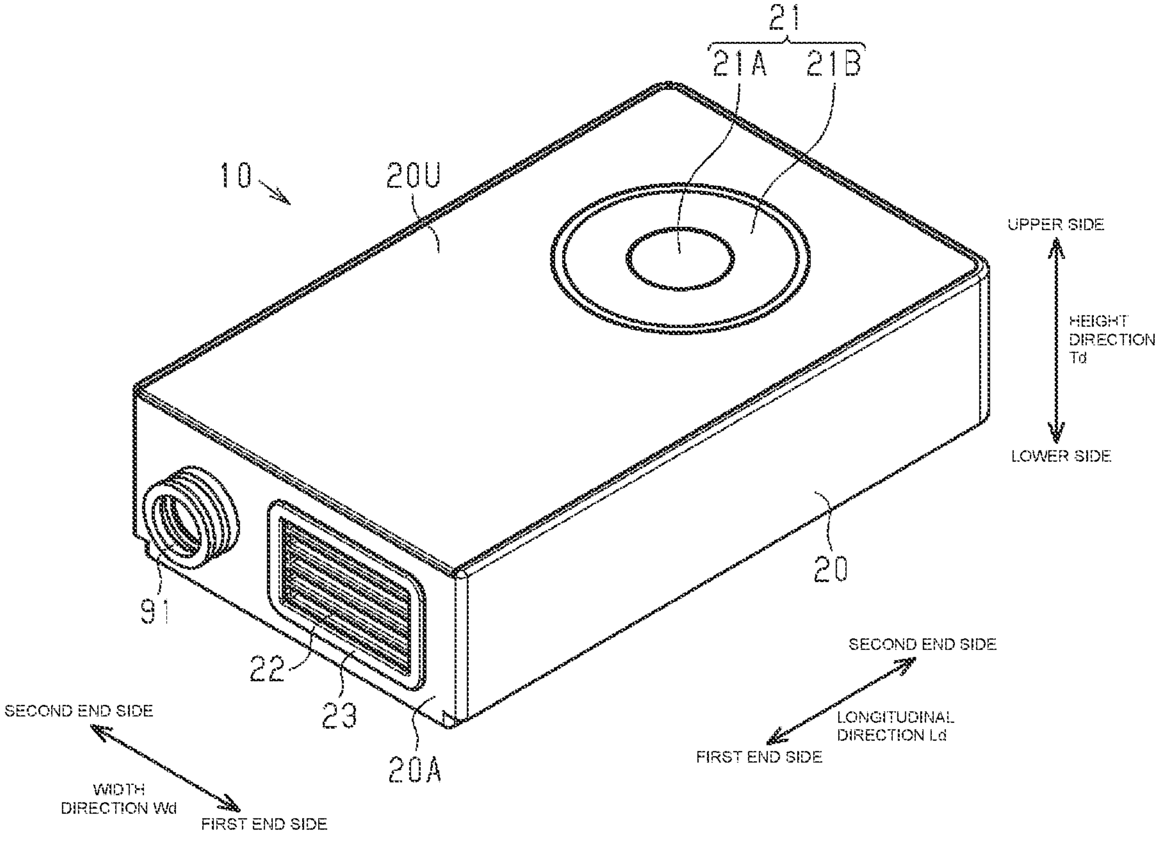
FIG. 1 is a perspective view illustrating a CPAP device.

As illustrated in FIG. 1, a CPAP device 10 includes a main body case 20 having a flat rectangular parallelepiped shape. In the following description, a thickness direction of the main body case 20 is referred to as a height direction Td. When viewed from the height direction Td, the length direction of the main body case 20 is referred to as a length direction Ld, and the short-side direction of the main body case 20 is referred to as a width direction Wd.

An operation unit 21 for operating the CPAP device 10 is provided on an upper-side surface 20U, which is a surface on the upper side in the height direction Td of the main body case 20. In this embodiment, the operation unit 21 is constituted of a switch 21A having a circular shape and a switch 21B having an annular shape. The switch 21B is disposed in such a manner as to surround the switch 21A. Both the switch 21A and the switch 21B are push button switches, and by operating these switches, it is possible to turn on and off a power supply of the CPAP device 10, change settings, and the like.

An inhalation port 22 for introducing air from the outside to the inside of the main body case 20 is opened in a first end surface 20A, which is an end surface on a first end side in the length direction Ld of the main body case 20. A filter 23 for filtering out dust and the like contained in the air to be introduced into the main body case 20 is attached to the inhalation port 22.

Figure 2:
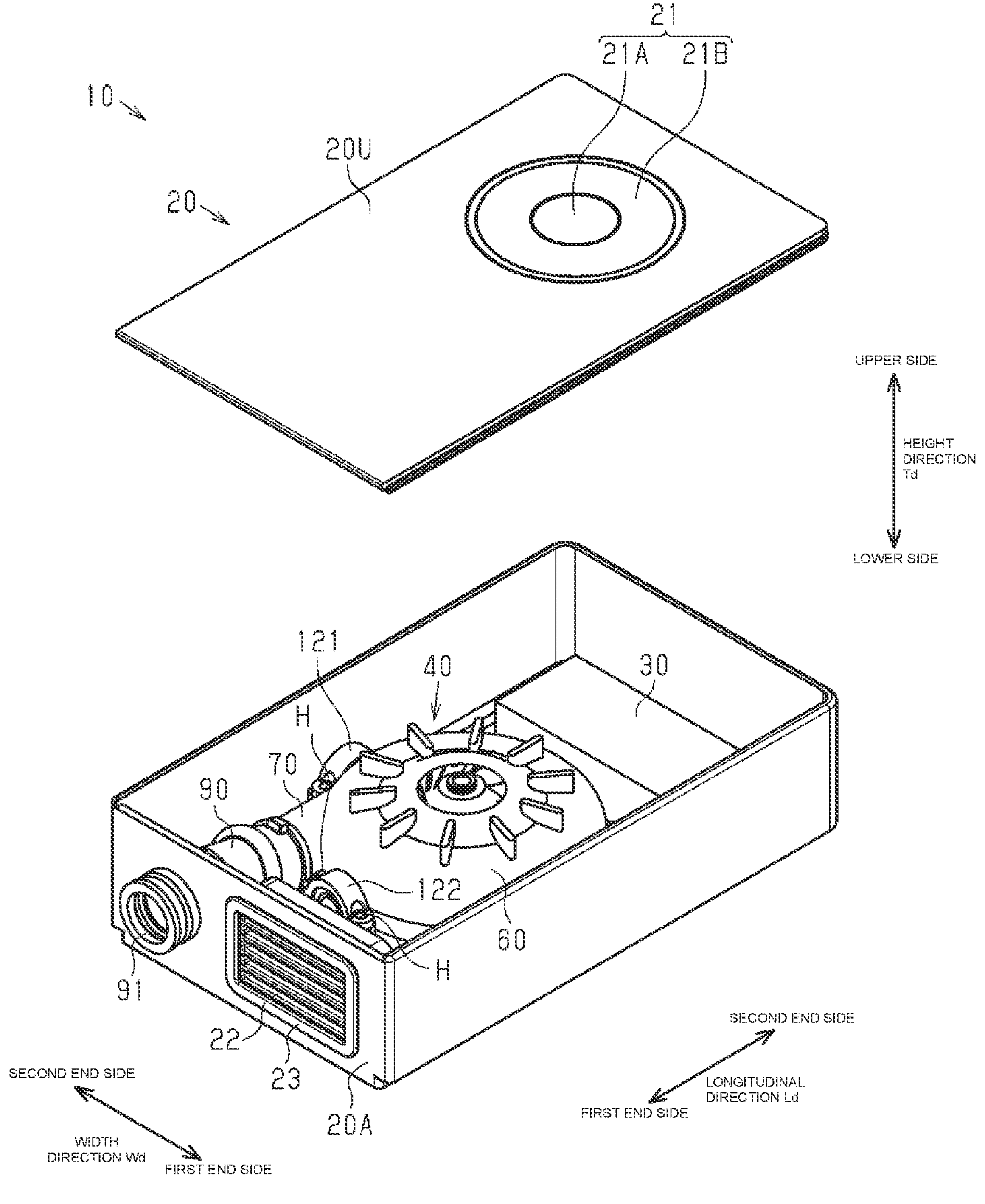
FIG. 2 is an exploded perspective view in which a CPAP device is exploded and illustrated.
Figure 3:
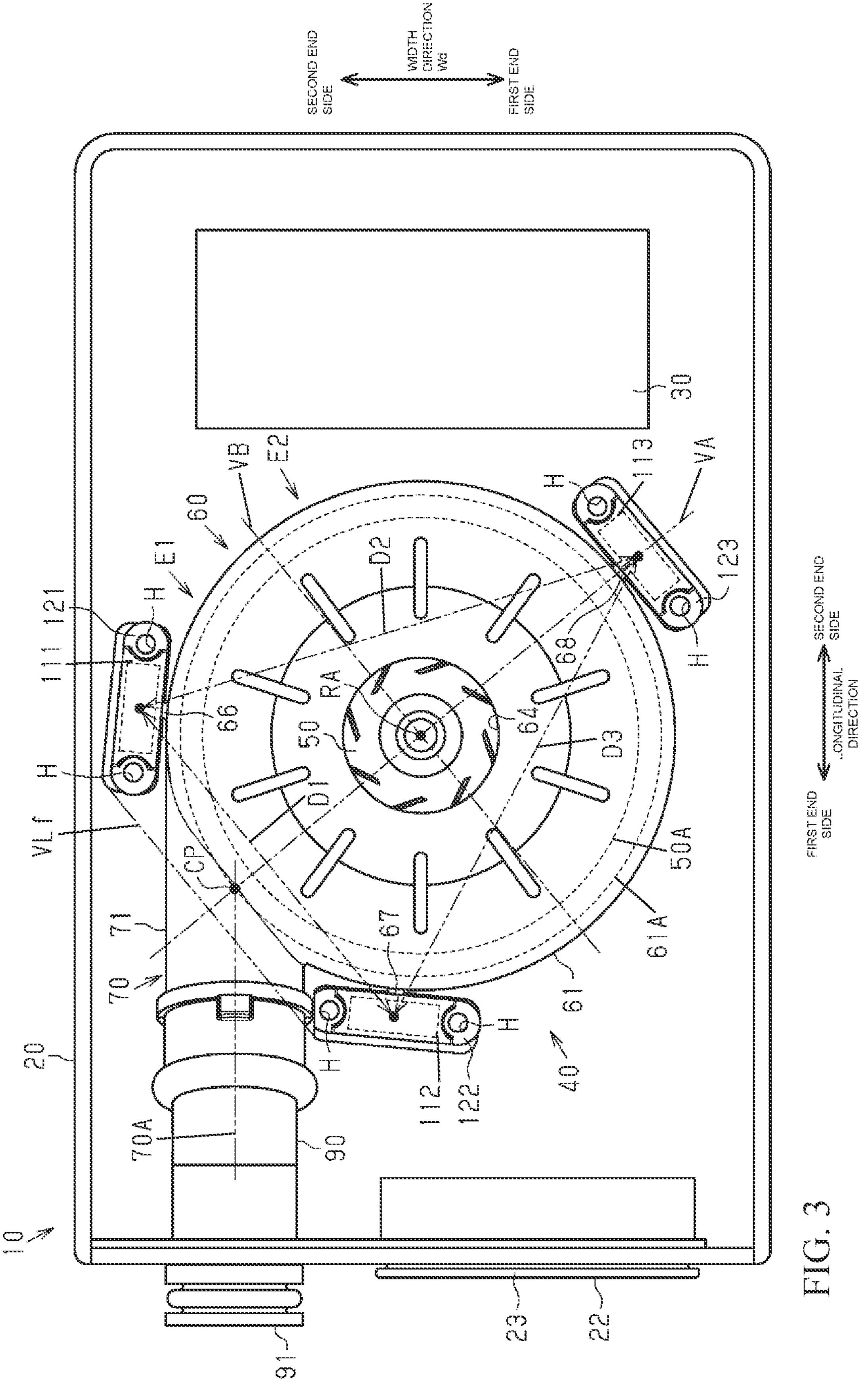
FIG. 3 is a top view illustrating a CPAP device.

As illustrated in FIG. 2, a control unit 30 is housed inside the main body case 20. The control unit 30 is disposed on a second end side relative to the center in the length direction Ld. The control unit 30 includes a control substrate and the like, and converts an operation of the operation unit 21 into an electric signal to control the CPAP device 10. In FIGS. 2 and 3, the control unit 30 is schematically illustrated as having a rectangular parallelepiped shape.

Figure 4:
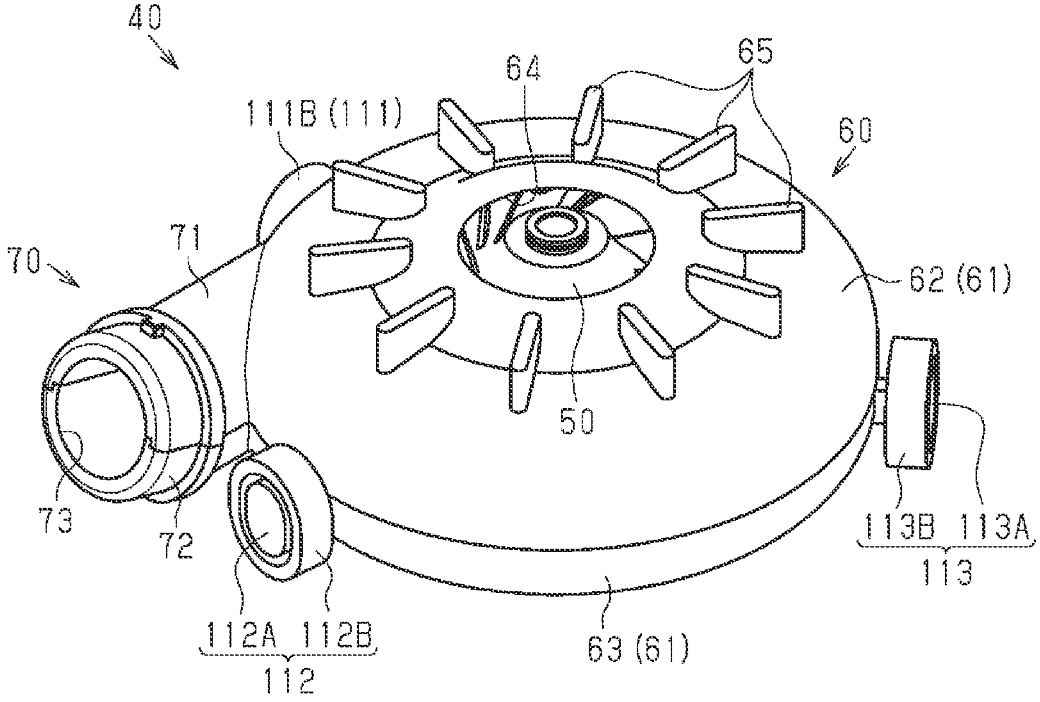
FIG. 4 is a perspective view illustrating a blower of a CPAP device.

As illustrated in FIG. 2, a blower 40 is housed inside the main body case 20. The blower 40 is disposed on the first end side relative to the control unit 30 in the length direction Ld. As illustrated in FIG. 4, the blower 40 is roughly divided into a fan unit 60 housing a fan 50 therein, and a delivery tube 70 through which air sent from the fan 50 passes.

As illustrated in FIG. 4, a fan case 61 of the fan unit 60 has a circular shape when viewed from the height direction Td. The fan case 61 includes an upper fan case 62 and a lower fan case 63.

Figure 5:
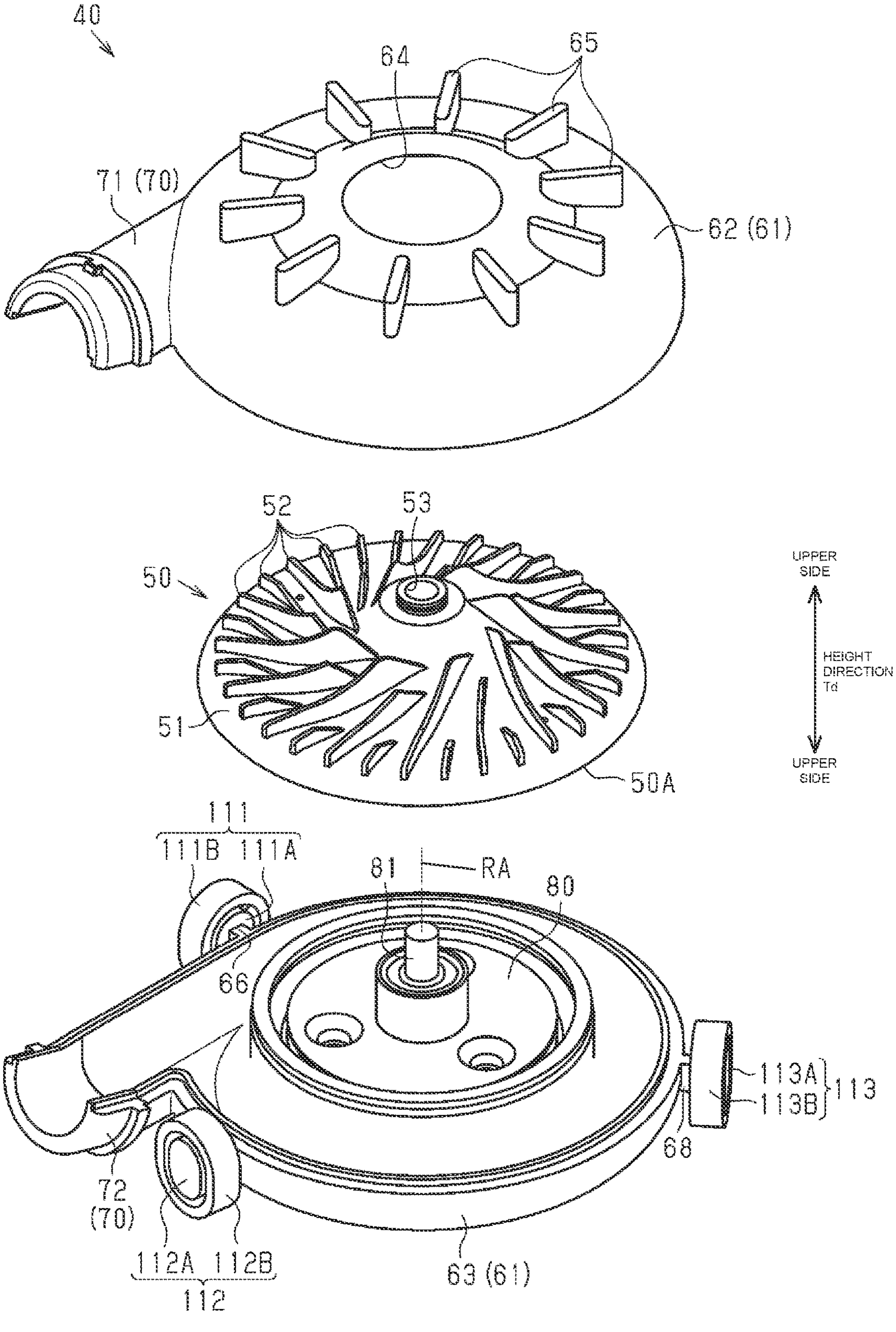
FIG. 5 is an exploded perspective view in which a blower of a CPAP device is exploded and illustrated.

As illustrated in FIG. 5, the upper fan case 62 has a circular bowl shape. In the center of the upper fan case 62, an introduction port 64 for inhaling air from the outside to the inside of the fan unit 60 is opened. The introduction port 64 has a circular shape in a plan view. A projection wall 65 having a plate shape projects upward from an outer surface on the upper side of the upper fan case 62. A plurality of the projection walls 65 is provided, and in the present embodiment, ten projection walls 65 are provided. The projection wall 65 extends in a radial direction of the upper fan case 62. The projection walls 65 are arranged at equal intervals in the circumferential direction at the outer side portion in the radial direction of the introduction port 64. Accordingly, the plurality of projection walls 65 is radially arranged when viewed from the height direction Td.

The lower fan case 63 has an annular shape when viewed from the height direction Td. The outside diameter of the lower fan case 63 is equal to the outside diameter of a lower edge of the upper fan case 62. A motor 80 is fitted into a hole at the center of the lower fan case 63. The lower end of the motor 80 is located on the upper side relative to the lower end of the lower fan case 63 in the height direction Td. That is, the motor 80 is not in contact with the main body case 20, and is supported by the lower fan case 63. A rotation shaft 81 of the motor 80 extends upward from the center of the motor 80.

The lower fan case 63 has a substantial U shape in a cross section orthogonal to the radial direction. The lower fan case 63 is fitted to the lower side of the upper fan case 62 to face each other. The upper fan case 62 and the lower fan case 63 define a housing space.

The fan 50 configured to send air by the rotation thereof is disposed in the housing space. The fan 50 is constituted of a holding plate 51 and a plurality of blades 52. The holding plate 51 has a substantial disk shape. An insertion hole 53 passes through the center of the holding plate 51. A tip end portion of the rotation shaft 81 of the motor 80 is fixed to the insertion hole 53. At a surface on the upper side of the holding plate 51, the plurality of blades 52 projects upward. The blade 52 has a plate shape. The blade 52 extends toward the outer side portion from the inner side in the radial direction of the holding plate 51. In this embodiment, the blades 52 having different extension lengths are provided. The blades 52 are arranged at equal intervals in the circumferential direction of the holding plate 51. Accordingly, the plurality of blades 52 is radially arranged when viewed from the height direction Td. Outer side ends in the radial direction of the blades 52 are each located on the same virtual circle centered on the center of the holding plate 51.

As illustrated in FIG. 4, the delivery tube 70 having a circular tube shape is connected to the fan unit 60. As illustrated in FIG. 5, the delivery tube 70 is constituted of an upper tube portion 71 and a lower tube portion 72. The upper tube portion 71 extends in a tangential direction of the circular-shaped upper fan case 62. When viewed from the extending direction of the upper tube portion 71, the upper tube portion 71 has an upwardly-convexed arc shape. That is, the upper tube portion 71 constitutes an upper half of the circular tube-shaped delivery tube 70. In the present embodiment, the upper tube portion 71 is integrally molded with the upper fan case 62.

The lower tube portion 72 extends in a tangential direction of the annular-shaped lower fan case 63. The extension length of the lower tube portion 72 is equal to that of the upper tube portion 71. When viewed from the extending direction of the lower tube portion 72, the lower tube portion 72 has a downward-convexed arc shape. That is, the lower tube portion 72 constitutes a lower half of the circular tube-shaped delivery tube 70. In the present embodiment, the lower tube portion 72 is integrally molded with the lower fan case 63.

As illustrated in FIG. 4, the lower tube portion 72 is fitted to the lower side of the upper tube portion 71 to face each other. A space inside the tube defined by the upper tube portion 71 and the lower tube portion 72 communicates with the housing space of the fan case 61. Air sent out from the fan unit 60 flows through this space inside the tube. An opening of the delivery tube 70 on the opposite side to the side connected to the fan unit 60 is a delivery port 73 for the delivery of the air from the blower 40 to the outside. As illustrated in FIG. 3, in the present embodiment, when viewed from the height direction Td, a connection point CP between the fan unit 60 and the delivery tube 70 is an intersection of a center axis line 70A, which passes through the center in the width direction Wd of the delivery tube 70 and extends in the extending direction of the delivery tube 70, and an outside diameter circle 61A of the housing space of the fan case 61.

As illustrated in FIG. 3, a discharge tube 90 for discharging air from the inside of the main body case 20 to the outside is connected to the delivery tube 70. The discharge tube 90 has a circular tube shape. The discharge tube 90 covers a portion of the delivery tube 70 on the first end side in the length direction Ld from the outer side portion in the radial direction.

As illustrated in FIG. 2, the discharge tube 90 passes through the first end surface 20A of the main body case 20 and extends in the length direction Ld.

Accordingly, an end of the discharge tube 90 on the first end side in the length direction Ld is located at an outer side portion of the main body case 20. An opening on the first end side in the length direction Ld of the discharge tube 90 is a discharge port 91 for discharging air from the inside to the outside of the main body case 20.

A support structure of the blower 40 in the main body case 20 will be described below.

As illustrated in FIG. 5, a first projection 66 projects toward an outer side portion in the radial direction from the outer surface of the lower fan case 63. As illustrated in FIG. 3, when viewed from the height direction Td, the first projection 66 is located on the side of the connection point CP between the fan unit 60 and the delivery tube 70 relative to a rotation axis RA of the fan 50 in the fan unit 60. In the present embodiment, the first projection 66 is disposed at a position near a side surface on the second end side in the width direction Wd of the main body case 20. In the present embodiment, the extending direction of the rotation axis RA coincides with the height direction Td.

As illustrated in FIG. 5, an inner portion 111A of a first damper 111 made of rubber is attached to the first projection 66. The inner portion 111A has a substantially elliptical shape slightly longer in the height direction Td when viewed from a projecting direction of the first projection 66. A recess (not illustrated) is provided in the inner portion 111A, and the first projection 66 and the first damper 111 are fixed by inserting the first projection 66 into the recess. At an outer side portion in the radial direction of the inner portion 111A, an outer portion 111B of the first damper 111 is disposed. The outer portion 111B has an elliptical ring shape surrounding the inner portion 111A from the outside. In the first damper 111, the inner portion 111A and the outer portion 111B are coupled to each other at a plurality of positions in the circumferential direction. In other words, the inner portion 111A and the outer portion 111B are separated from each other at a position where they are not coupled to each other so as to be relatively movable.

As illustrated in FIG. 3, a second projection 67 projects toward an outer side portion in the radial direction from the outer surface of the lower fan case 63 in the fan unit 60. When viewed from the height direction Td, the second projection 67 is located on the side of the connection point CP between the fan unit 60 and the delivery tube 70 relative to the rotation axis RA of the fan 50 in the fan unit 60. The second projection 67 is disposed on the opposite side to the first projection 66 across the center axis line 70A of the delivery tube 70.

As illustrated in FIG. 5, a second damper 112 made of rubber is attached to the second projection 67. The constitution of the second damper 112 is the same as that of the first damper 111. To be specific, the second damper 112 is constituted of an inner portion 112A and an outer portion 112B.

A third projection 68 projects toward an outer side portion in the radial direction from the outer surface of the lower fan case 63 when viewed from the height direction Td. As illustrated in FIG. 3, when viewed from the height direction Td, the third projection 68 is located on the opposite side to the connection point CP between the fan unit 60 and the delivery tube 70 relative to the rotation axis RA of the fan 50 in the fan unit 60.

A third damper 113 made of rubber is attached to the third projection 68. The constitution of the third damper 113 is the same as that of the first damper 111. To be specific, the third damper 113 is constituted of an inner portion 113A and an outer portion 113B.

As illustrated in FIG. 3, a first support member 121 is attached to the bottom of the main body case 20. The first support member 121 is formed substantially in a plate shape. The first support member 121 is disposed near a side wall on the second end side in the width direction Wd of the main body case 20. Threaded holes H are provided at both ends in an extension direction of the first support member 121. The first support member 121 is fixed to the main body case 20 by screwing screws (not illustrated) into the threaded holes H. In the first support member 121, there is a hole passing through in the thickness direction of the first support member 121. The first damper 111 of the fan unit 60 described above is fitted into the hole of the first support member 121. That is, the first support member 121 is interposed between the main body case 20 and the fan unit 60, and supports the fan unit 60 in the main body case 20.

A second support member 122 is attached to the bottom of the main body case 20. The constitution of the second support member 122 is the same as that of the first support member 121. The second support member 122 is disposed near a side wall on the first end side in the length direction Ld of the main body case 20. The second damper 112 of the fan unit 60 described above is fitted into a hole passing through in the thickness direction of the second support member 122. That is, the second support member 122 is interposed between the main body case 20 and the fan unit 60, and supports the fan unit 60 in the main body case 20.

A third support member 123 is attached to the bottom surface of the main body case 20. The constitution of the third support member 123 is the same as that of the first support member 121. The third support member 123 is disposed near a side wall on the first end side in the width direction Wd of the main body case 20. The third damper 113 of the fan unit 60 described above is fitted into a hole passing through in the thickness direction of the third support member 123. That is, the third support member 123 is interposed between the main body case 20 and the fan unit 60, and supports the fan unit 60 in the main body case 20.

Next, the arrangement of the three support members will be described in detail. The first support member 121 is disposed as corresponding to the first damper 111 of the fan unit 60. As described above, the first damper 111 is attached to the first projection 66. Accordingly, the first support member 121 is disposed at an outer side portion of the fan unit 60 when viewed from the height direction Td. When viewed from the height direction Td, the first support member 121 is located on the side of the connection point CP between the fan unit 60 and the delivery tube 70 relative to the rotation axis RA of the fan 50 in the fan unit 60.

The second support member 122 is disposed as corresponding to the second damper 112 of the fan unit 60. As described above, the second damper 112 is attached to the second projection 67. Accordingly, the second support member 122 is located at an outer side portion of the fan unit 60 when viewed from the height direction Td. When viewed from the height direction Td, the second support member 122 is located on the side of the connection point CP between the fan unit 60 and the delivery tube 70 relative to the rotation axis RA of the fan 50. When viewed from the height direction Td, the second support member 122 is disposed on the opposite side to the first support member 121 across the connection point CP. Accordingly, the first support member 121 and the second support member 122 are disposed to pinch the blower 40 therebetween. Specifically, when viewed from the height direction Td, a boundary VB of the blower 40 is taken as a straight line that is orthogonal to a straight line VA passing through the rotation axis RA of the fan 50 and the connection point CP and passes through the rotation axis RA of the fan 50. In this case, with the boundary VB as a boundary, a region on the connection point CP side is defined as a first region E1, and a region on the opposite side to the connection point CP is defined as a second region E2. In the present embodiment, the first support member 121 and the second support member 122 support the first region E1 of the fan unit 60 of the blower 40.

In this case, a large number of virtual line segments may be drawn between the first support member 121 and the second support member 122. Among the virtual line segments that may be drawn in this way, a virtual line segment farthest from the rotation axis RA is defined as a virtual line segment VLf. When viewed from the height direction Td, the virtual line segment VLf is in contact with the first support member 121 and the second support member 122 from the side opposite to the rotation axis RA in the direction in which the straight line VA extends. When viewed from the height direction Td, the virtual line segment VLf is located at an outer side portion in the radial direction relative to an outer edge 50A of the fan 50. That is, the virtual line segment VLf does not intersect the fan 50.

Many of the virtual line segments that may be drawn between the first support member 121 and the second support member 122 pass through on the rotation axis RA side relative to the connection point CP between the fan unit 60 and the delivery tube 70. Accordingly, the first support member 121 and the second support member 122 are disposed on the rotation axis RA side relative to the connection point CP, that is, are disposed to pinch the fan unit 60 of the blower 40. When viewed from the height direction Td, some of the virtual line segments that may be drawn between the first support member 121 and the second support member 122 do not intersect any of the fan 50 and the delivery tube 70.

The third support member 123 is disposed as corresponding to the third damper 113 of the fan unit 60. As described above, the third damper 113 is attached to the third projection 68. Accordingly, the third support member 123 is disposed at an outer side portion of the fan unit 60 when viewed from the height direction Td. When viewed from the height direction Td, the third support member 123 is located on the opposite side to the connection point CP between the fan unit 60 and the delivery tube 70 relative to the rotation axis RA of the fan 50. That is, the third support member 123 supports the fan unit 60 of the blower 40 in the second region E2. In particular, in the present embodiment, when viewed from the height direction Td, the third support member 123 is located at a position where the distance between the third support member 123 and the first support member 121 is equal to the distance between the third support member 123 and the second support member 122. In other words, the third support member 123 is disposed on the straight line VA passing through the rotation axis RA of the fan 50 and the connection point CP.

In this embodiment, as illustrated in FIG. 3, the distance between the support members is defined as the distance between the fixing centers of the support members, that is, the distance between the midpoints at the centers of the two threaded holes H of the support members. A first distance D1 as the distance between the first support member 121 and the second support member 122 is shorter than a second distance D2 as the distance between the first support member 121 and the third support member 123. The first distance D1 is shorter than a third distance D3 as the distance between the second support member 122 and the third support member 123. The second distance D2 is equal to the third distance D3. Thus, an isosceles triangle is formed by the three line segments for determining the distances between each of the support members. In this isosceles triangle, the equal sides are longer than the base. In the present embodiment, the fan unit 60 is supported to the main body case 20 only by three support members, and the fan unit 60 is not in direct contact with the main body case 20.

Next, the operations of the CPAP device 10 in the above-described embodiment will be described.

Figure 6:
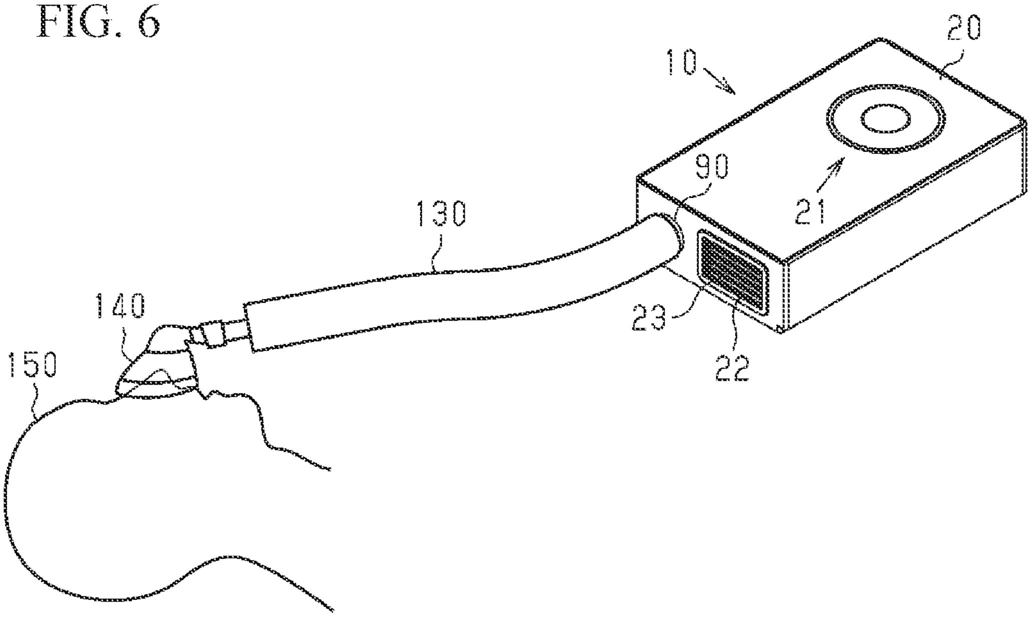
FIG. 6 is an explanatory diagram for explaining a usage state of a CPAP device.

As illustrated in FIG. 6, when the CPAP device 10 is used, a first end portion of a hose 130 is connected to the tip end portion of the discharge tube 90 projecting to the outside of the main body case 20. Then, a second end portion of the hose 130 is connected to a mask 140. The mask 140 is worn to cover the nose or mouth of a user 150, for example.

When the motor 80 is driven by the operation unit 21 of the CPAP device 10 being operated, the rotation shaft 81 of the motor 80 rotates. With the rotation of the rotation shaft 81, the fan 50 rotates taking the rotation axis RA as the rotation center. When the fan 50 rotates, air is sucked into the main body case 20 from the outside of the main body case 20 through the inhalation port 22. The air sucked into the main body case 20 through the inhalation port 22 is inhaled into the housing space of the fan unit 60 of the blower 40 from the introduction port 64. The air in the housing space of the fan unit 60 is sent out to the delivery tube 70 by the fan 50. The air delivered from the delivery port 73 of the delivery tube 70 passes through the discharge tube 90 to be discharged to the outside of the main body case 20. The air passes through the hose 130, and is delivered from the mask 140 to the user 150.

Next, effects of the CPAP device 10 in the above-described embodiment will be described.

(1) According to the above-described embodiment, when viewed from the height direction Td, the first support member 121 and second support member 122 are each disposed on the side of the connection point CP between the fan unit 60 and the delivery tube 70 relative to the rotation axis RA of the fan 50. The first support member 121 and second support member 122 are disposed to pinch the blower 40 therebetween. This makes it possible to suppress the vibrations of a portion of the fan unit 60 near the delivery tube 70. Thus, since the vibrations of the delivery tube 70 may be suppressed, it is also possible to suppress the transmission of the vibrations from the delivery tube 70 to the user 150 via the hose 130, the mask 140, and the like. As a result, the user 150 is unlikely to perceive the vibrations.

(2) According to the above-described embodiment, the delivery tube 70 is not supported to the main body case 20 by the support members. The delivery tube 70 is only connected to the discharge tube 90. Thus, even when the fan unit 60 vibrates, it is possible to suppress the transmission of the vibrations to the delivery tube 70 via the support members, the main body case 20, and the like.

(3) According to the above-described embodiment, when viewed from the height direction Td, the virtual line segment VLf farthest from the rotation axis RA among the virtual line segments that may be drawn between the first support member 121 and the second support member 122 does not intersect the fan 50. Due to this, portions of the fan unit 60 of the blower 40 in contact with the first support member 121 and the second support member 122 are close to the delivery tube 70 accordingly. Thus, by the support at a position close to the connection point CP between the delivery tube 70 and the fan unit, the transmission of the vibrations to the delivery tube 70 may be reliably suppressed.

(4) In the above-described configuration, because the fan unit 60 is firmly supported by the first support member 121 and the second support member 122, vibrations may occur in the fan unit 60 taking a virtual line segment that may be drawn between the first support member 121 and the second support member 122 as the axis in a case where the vibrations are assumed to occur in the fan unit 60. Of the virtual line segments, the virtual line segment VLf farthest from the rotation axis RA of the fan 50 does not intersect the fan 50. Therefore, when vibrations occur in the fan unit 60 taking the virtual line segment VLf as the axis, there is a high possibility that the entire fan 50 integrally vibrates. Accordingly, it is possible to suppress the occurrence of distortion or the like in the fan 50 when the fan 50 attempts to locally vibrates.

(5) In the above-described embodiment, when viewed from the height direction Td, some of the virtual line segments that may be drawn between the first support member 121 and the second support member 122 do not intersect any of the fan 50 and the delivery tube 70. This makes it possible to prevent a situation in which the vibrations of the fan unit 60 and the vibrations of the delivery tube 70 interfere with each other taking the virtual line segment as a boundary.

(6) According to the above-described embodiment, when viewed from the height direction Td, the first support member 121 and second support member 122 are disposed in the first region E1 on the side of the connection point CP between the fan unit 60 and the delivery tube 70 relative to the rotation axis RA. On the other hand, when viewed from the height direction Td, the third support member 123 is disposed in the second region E2 on the opposite side to the connection point CP between the fan unit 60 and the delivery tube 70 relative to the rotation axis RA. That is, when the blower 40 vibrates taking a virtual line segment connecting the first support member 121 and the second support member 122 as the axis, a side thereof where the vibrations become large is supported by the third support member 123. That is, the third support member 123 is disposed at a position where the vibrations of the blower 40 may be more effectively suppressed.

(7) In the above-described embodiment, when viewed from the height direction Td, only the third support member 123 is disposed as a support member on the opposite side to the connection point CP between the fan unit 60 and the delivery tube 70 relative to the rotation axis RA. That is, the support force is weaker on the side opposite to the delivery tube 70 side with the connection point CP as a reference. Accordingly, even when vibrations occur in the blower 40, the blower 40 is likely to vibrate on the side opposite to the delivery tube 70, and thus the vibrations on the delivery tube 70 side are minimized.

(8) According to the above-described embodiment, the second distance D2 between the first support member 121 and the third support member 123 is equal to the third distance D3 between the second support member 122 and the third support member 123. As a result, when a virtual straight line passing through the rotation axis RA is drawn from the fixing center of the third support member 123, it is possible to suppress the occurrence of distortion in the fan unit 60 due to the uneven vibrations of the blower 40 on both sides of the virtual straight line.

(9) According to the above-described embodiment, the third support member 123 is disposed on the straight line VA passing through the rotation axis RA of the fan 50 and the connection point CP. Thus, the vibrations absorbed by the third support member 123 are unlikely to be transmitted to the delivery tube 70 by fixing the blower 40 at a portion farthest from the delivery tube 70 with the third support member 123.

(10) According to the above-described embodiment, each of the three support members is disposed at the outer side portion of the fan unit 60 when viewed from the height direction Td. The three support members support the blower 40 from the outside. As a result, even in a case where the blower 40 vibrates in a direction orthogonal to the rotation axis RA when the fan 50 rotates, it is easy to suppress the vibrations in such a direction.

(11) According to the above-described embodiment, the first damper 111 is supported by the first support member 121. The first damper 111 is constituted of the inner portion 111A and the outer portion 111B. When the inner portion 111A vibrates, the vibrations transmitted to the outer portion 111B are reduced. With this, the vibrations of the fan unit 60 are attenuated before being transmitted to the first support member 121 via the first damper 111. The same applies to the second damper 112 and the third damper 113 in this respect.

The above-described embodiment may be modified as follows. The above-described embodiment and the following modifications may be combined and implemented within a range in which there is no technical contradiction.

In the above-described embodiment, the CPAP device 10 may include a humidifier. For example, a humidifier may be attached to the discharge tube 90 of the main body case 20, and the hose 130 may be attached to the discharge side of the humidifier. Further, for example, a humidifier may be housed inside the main body case 20, and the humidifier may be arranged between the delivery tube 70 and the discharge tube 90. In this case, the air delivered from the delivery tube 70 is humidified by the humidifier and reaches the user 150 from the discharge tube 90 through the hose 130.

In the above-described embodiment, the shape of the main body case 20 is not limited to the example of the embodiment described above. The shape may take a polygonal shape or a spherical shape. The shapes and positions of the inhalation port 22, the discharge tube 90, and the like of the main body case 20 are not limited to the example of the above-described embodiment. For example, the shape of the inhalation port 22 may be circular, and the discharge tube 90 may pass through an end surface facing the opposite side to the first end surface 20A, where the inhalation port 22 is located.

In the above-described embodiment, the shape of the blower 40 is not limited to the example of the embodiment described above. For example, in the case where the housing space of the fan case 61 of the fan unit 60 for housing the fan 50 has a circular shape when viewed from the height direction Td, the outer shape of the fan case 61 may take a rectangular parallelepiped shape or a polygonal shape. Further, for example, the delivery tube 70 may extend in such a manner as to widen the inside diameter thereof, or may be curved.

In the above-described embodiment, the locations where the first support member 121 and the second support member 122 are disposed are not limited to the example of the embodiment described above. For example, when viewed from the height direction Td, it is sufficient that the locations thereof are on the side of the connection point CP between the fan unit 60 and the delivery tube 70 relative to the rotation axis RA in the circumferential direction of the fan case 61. As the first support member 121 and the second support member 122 are disposed farther away from the delivery tube 70, it is possible to suppress the transmission of vibration to the delivery tube 70 via these support members.

For example, the first support member 121 and the second support member 122 may be disposed in such a manner as to pinch the delivery tube 70 when viewed from the height direction Td. In this case, when viewed from the height direction Td, any of the virtual line segments that may be drawn between the first support member 121 and the second support member 122 does not intersect the fan 50. When the first support member 121 and the second support member 122 are disposed as in this modification example, the distortion or the like of the fan 50 may be suitably suppressed.

Figure 7:
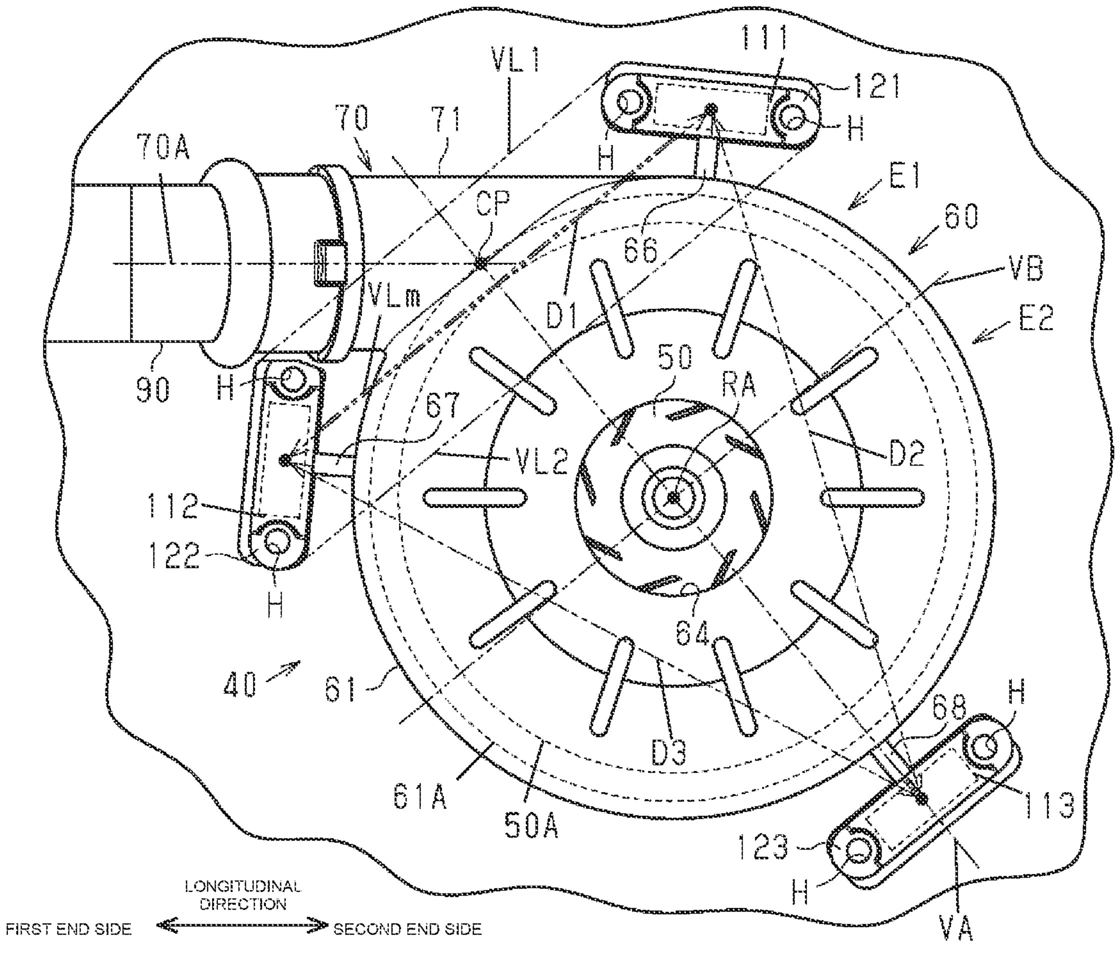
FIG. 7 is a top view illustrating part of a CPAP device of a modification example.

Further, for example, in a modification example illustrated in FIG. 7, when viewed from the height direction Td, the first support member 121 and the second support member 122 are set far from the rotation axis RA in terms of the locations in the radial direction of the fan 50. Specifically, as compared with the embodiment illustrated in FIG. 3, the amount of extension of each of the first projection 66 and the second projection 67 is large toward an outer side portion in the radial direction of the fan 50. In this case, of virtual line segments that may be drawn between the first support member 121 and the second support member 122, a virtual line segment farthest from the rotation axis RA among the virtual line segments orthogonal to the straight line VA is taken as a first virtual line segment VL1, and a virtual line segment closest to the rotation axis RA is taken as a second virtual line segment VL2. A virtual line segment passing through the center between the first virtual line segment VL1 and the second virtual line segment VL2 in the direction in which the straight line VA extends, is taken as an intermediate virtual line segment VLm. That is, the intermediate virtual line segment VLm is an intermediate virtual line segment equally distanced from the first virtual line segment VL1 and the second virtual line segment VL2. In the example illustrated in FIG. 7, the intermediate virtual line segment VLm intersects neither the fan 50 nor the delivery tube 70 when viewed from the height direction Td. This makes it possible to prevent a situation in which the vibrations of the fan unit 60 and the vibrations of the delivery tube 70 interfere with each other taking the intermediate virtual line segment VLm as a boundary.

In the above-described embodiment, all of the virtual line segments that may be drawn between the first support member 121 and the second support member 122 may intersect the fan 50. Any of the virtual line segments may intersect none of the fan 50 and the delivery tube 70.

In the above-described embodiment, the location where the third support member 123 is disposed is not limited to the example of the embodiment described above. For example, when viewed from the height direction Td, it is sufficient that the location is on the side opposite to the connection point CP between the fan unit 60 and the delivery tube 70 relative to the rotation axis RA. It is preferable that the second distance D2 between the first support member 121 and the third support member be longer than the first distance D1 between the first support member 121 and the second support member 122, and the third distance D3 between the second support member 122 and the third support member 123 be longer than the first distance D1 between the first support member 121 and the second support member 122, in order to suppress the vibrations of the entire fan unit 60. However, the third support member 123 may be disposed at such a location that causes the second distance D2 to be shorter than the first distance D1, or may be disposed at such a location that causes the third distance D3 to be shorter than the first distance D1. Furthermore, the third support member 123 may be disposed in such a manner that the second distances D2 and the third distances D3 are different from each other.

For example, it is not necessary for the third support member 123 to be located on the straight line VA passing through the rotation axis RA and the connection point CP. In this case as well, when viewed from the height direction Td, it is sufficient that the location is at least on the side opposite to the connection point CP relative to the rotation axis RA, in other words, the location is within the second region E2.

In the above-described embodiment, each support member is fixed to the bottom of the main body case 20, but a location where the support member is fixed to the main body case 20 is not limited to the example of the embodiment described above. For example, each support member may be fixed to a side surface, a lid surface, or the like of the main body case 20.

In the above-described embodiment, the constitution of each of the support members is not limited to the example of the embodiment described above. For example, the fan unit 60 may be provided with none of the projections and dampers, and may be supported to the main body case 20 by directly fixing the fan case 61 with bolts. In this case, the bolt functions as a support member.

In the above-described embodiment, the number of locations at which the blower 40 is supported may be four or more. For example, the fan unit 60 may be supported by the fourth support member. In this case, when viewed from the direction of the rotation axis RA of the fan 50, it is preferable that the fourth support member be disposed on the side of the connection point CP between the fan unit 60 and the delivery tube 70 in terms of suppressing the vibrations on the delivery tube 70 side of the fan unit 60.

In the above-described embodiment, the extending direction of each projection is not limited to the direction extending toward the outer side portion when viewed from the height direction Td, and may extend in the height direction Td, for example. For example, the first damper 111 may be disposed on the upper side of the fan unit 60, the second damper 112 may be disposed on the lower side of the fan unit 60, and the first support member 121 and the second support member 122 may support each of the dampers. In this case, the first support member 121 and the second support member 122 are disposed to pinch the fan unit 60 therebetween in the height direction Td. Further, any or all of the first damper 111, second damper 112, and third damper 113, may have different shapes or forms than those illustrated with respect to the above-described embodiment.

Figure 8A:
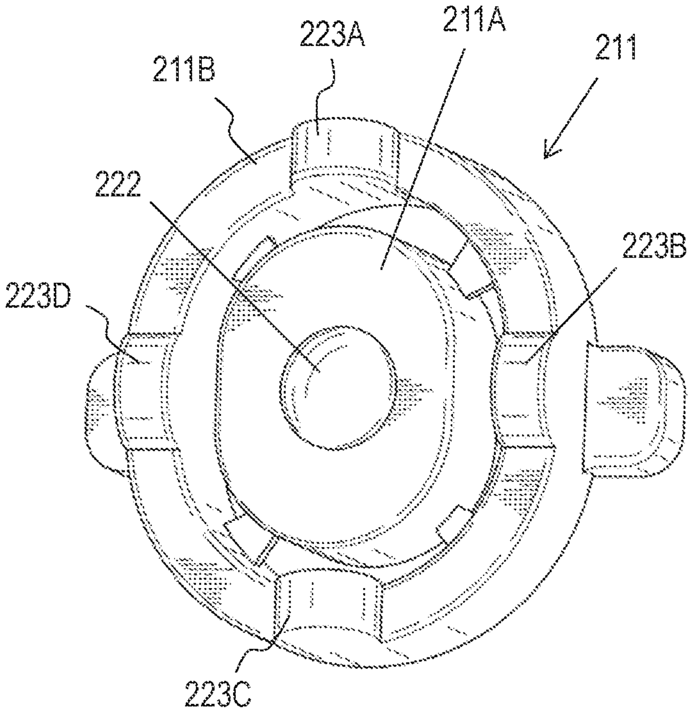
FIG. 8A is an inner perspective view of a damper according to a modification example.
Figure 8B:
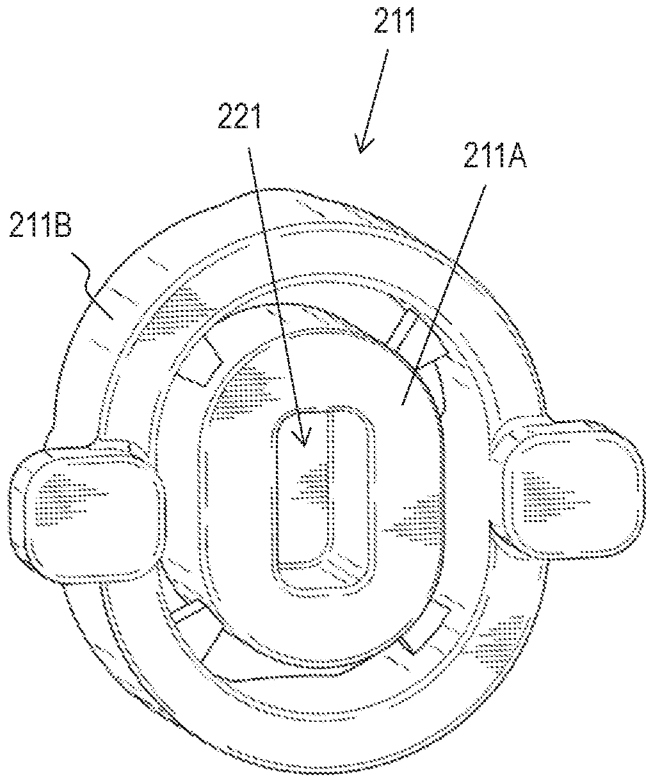
FIG. 8B is an outer perspective view of a damper according to the modification example.
Figure 9:
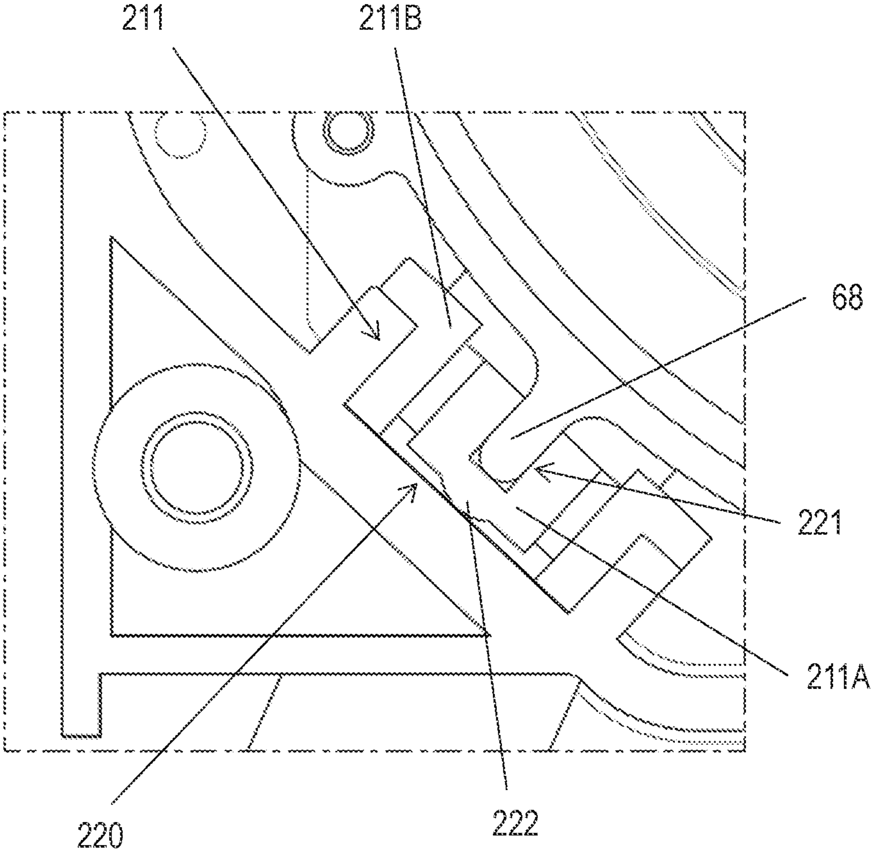
FIG. 9 is a top view illustrating a blower of a CPAP device housed in a case with a dampers of the modification example.

For example, any or all of the dampers 111, 112, 113 may be constituted according to an example modification damper 211 illustrated in FIGS. 8A and 8B. Except as noted, the configuration of the modification example of damper 211 is similar to that of the dampers 111, 112, 113, and a description of similar portions is omitted. An inner portion 211A of the damper 211 has a recess on its inside in which a projection 66, 67, 68 is fixed by inserting the projection 66, 67, 68 into the recess 221. An outside of the inner portion has a protrusion 222. Similarly, an outer portion 211B of the modification example of damper 211 has a plurality of protrusions 223A, 223B, 223C, 223D equally spaced circumferentially around an outside of the outer portion 211B that generally extend radially away from the fan unit 60. While the protrusion 222, 223A, 223B, 223C, 223D are illustrated as having a rounded, the protrusions may be other shapes. Further, a fewer or greater number of protrusions may be provided on the damper 211 and may be provided at different spacings. FIG. 9 illustrates a top view of a CPAP device where damper 113 is constituted as the modification example of damper 211, fixed to projection 68. As seen in FIG. 9, the protrusions 222, 223A, 223B, 223C, 223D contact a housing wall surface 220 against which the CPAP device is mounted in main body case 20. According to this modification example, the housing wall surface 220 only contacts the damper 211 via the protrusions 222, 223A, 223B, 223C, 223D. Therefore, the contact area between the housing wall surface 220 and the damper 211 is reduced. By reducing the contact area, vibration transmission to any housing, the main body case 20, and other elements therein can be suppressed. Thus, operating noise during blower operation can also be suppressed.

10 CPAP DEVICE
20 MAIN BODY CASE
40 BLOWER
50 FAN
60 FAN UNIT
70 DELIVERY TUBE
80 MOTOR
90 DISCHARGE TUBE
111 FIRST DAMPER

112 SECOND DAMPER
113 THIRD DAMPER
121 FIRST SUPPORT MEMBER
122 SECOND SUPPORT MEMBER
123 THIRD SUPPORT MEMBER
CP CONNECTION POINT
RA ROTATION AXIS
VL VIRTUAL LINE SEGMENT

The invention claimed is:

1. A continuous positive airway pressure device, comprising:

a main body case;

a blower housed inside the main body case; and three or more dampers, wherein the blower comprises a fan unit housing a fan configured to send air by being rotated, a delivery tube through which the air sent from the fan passes, and three or more projections that project radially away from the fan unit and that are respectively fixed to the three or more dampers, and wherein the three or more dampers each comprise one or more protrusions that protrude from the dampers, radially away from the fan unit, and directly contact a housing wall surface of the main body case without an intervening support member fixed to the main body case.

2. The continuous positive airway pressure device according to claim 1, wherein the one or more protrusions are rounded.

3. The continuous positive airway pressure device according to claim 1, wherein each of the three or more dampers comprises:

an inner portion having a recess in which the respective projection is fixed, and having one of the one or more protrusions; and an outer portion having an elliptical ring shape surrounding the inner portion from the outside, and coupled to the inner portion at a plurality of positions in a circumferential direction.

4. The continuous positive airway pressure device according to claim 3, wherein the outer portion comprises four of the one or more protrusions, equally spaced circumferentially around an outside of the outer portion.

5. The continuous positive airway pressure device according to claim 1, wherein the dampers are rubber.

6. The continuous positive airway pressure device according to claim 1, further comprising:

three or more support members, respectively fixed to the three or more dampers, and configured to support the blower inside the main body case, wherein in a view from a direction of a rotation axis of the fan:

first and second support members of the support members are disposed to pinch the blower on a side of a connection point between the fan unit and the delivery tube relative to the rotation axis, and a third support member different from the first and second support members of the support members is disposed on a side opposite to the connection point relative to the rotation axis.

7. The continuous positive airway pressure device according to claim 6, wherein in a view from the rotation axis direction of the fan, the first support member and the second support member are disposed to pinch the fan unit, and the support members are not disposed between the delivery tube and the main body case.

8. The continuous positive airway pressure device according to claim 6, wherein in a view from the rotation axis direction of the fan, of virtual line segments allowed to be drawn between the first support member and the second support member, a virtual line segment farthest from the rotation axis does not intersect the fan.

9. The continuous positive airway pressure device according to claim 6, wherein in a view from the rotation axis direction of the fan, of the virtual line segments allowed to be drawn between the first support member and the second support member, at least some of the virtual line segments do not intersect any of the fan and the delivery tube.

10. The continuous positive airway pressure device according to claim 6, wherein in a view from the rotation axis direction of the fan, in a case that the blower is divided into a first region on the connection point side and a second region on a side opposite to the connection point by a boundary being a straight line passing through the rotation axis and orthogonal to another straight line passing through the rotation axis and the connection point, the first support member and the second support member support the blower in the first region, the third support member supports the blower in the second region, and a distance between the third support member and the first support member and a distance between the third support member and the second support member are both longer than a distance between the first support member and the second support member.

11. The continuous positive airway pressure device according to claim 6, wherein the third support member is disposed on a straight line passing through the connection point and the rotation axis.

12. The continuous positive airway pressure device according to claim 6, wherein all of the support members are disposed at outer side portions of the fan unit in a view from the rotation axis direction of the fan.

13. The continuous positive airway pressure device according to claim 1, wherein the housing wall surface and each of the dampers are only in contact via the respective protrusion.

14. The continuous positive airway pressure device according to claim 1, wherein each of the three or more dampers comprises an inner portion having one of the one or more protrusions, and an outer portion surrounding the inner portion from the outside.

* * * * *